(12) United States Patent
Mao et al.

(10) Patent No.: US 12,648,916 B2
(45) Date of Patent: Jun. 9, 2026

(54) POLYMERIC NANOPARTICLE COMPOSITIONS FOR ENCAPSULATION AND SUSTAINED RELEASE OF PROTEIN THERAPEUTICS

(71) Applicant: THE JOHNS HOPKINS UNIVERSITY, Baltimore, MD (US)

(72) Inventors: Hai-Quan Mao, Baltimore, MD (US); Sashank Reddy, Baltimore, MD (US); Xiyu Ke, Baltimore, MD (US); Chenhu Qiu, Baltimore, MD (US); Daniel Lucena Comingues, Baltimore, MD (US); Gregory P. Howard, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1062 days.

(21) Appl. No.: 16/965,761

(22) PCT Filed: Jan. 29, 2019

(86) PCT No.: PCT/US2019/015498
§ 371 (c)(1),
(2) Date: Jul. 29, 2020

(87) PCT Pub. No.: WO2019/148147
PCT Pub. Date: Aug. 1, 2019

(65) Prior Publication Data
US 2021/0030692 A1      Feb. 4, 2021

Related U.S. Application Data

(60) Provisional application No. 62/623,018, filed on Jan. 29, 2018.

(51) Int. Cl.
| | |
|---|---|
| *A61K 9/51* | (2006.01) |
| *A61K 38/47* | (2006.01) |
| *A61K 39/00* | (2006.01) |
| *A61K 39/395* | (2006.01) |

(52) U.S. Cl.
CPC .......... *A61K 9/5153* (2013.01); *A61K 9/5192* (2013.01); *A61K 38/47* (2013.01); *A61K 39/395* (2013.01); *A61K 2039/505* (2013.01)

(58) Field of Classification Search
CPC ............. A61K 9/00; A61K 9/10; A61K 47/61
USPC ....................................................... 424/489
See application file for complete search history.

(56) References Cited

U.S. PATENT DOCUMENTS

| | | | |
|---|---|---|---|
| 5,399,363 | A | 3/1995 | Liversidge et al. |
| 5,466,468 | A | 11/1995 | Schneider et al. |
| 5,543,158 | A | 8/1996 | Gref et al. |
| 5,580,579 | A | 12/1996 | Ruddy et al. |
| 5,626,001 | A | 5/1997 | Belec |
| 5,629,001 | A | 5/1997 | Michael et al. |
| 5,641,515 | A | 6/1997 | Ramtoola |
| 5,725,871 | A | 3/1998 | Illum |
| 5,756,353 | A | 5/1998 | Debs |
| 5,780,045 | A | 7/1998 | McQuinn et al. |
| 5,792,451 | A | 8/1998 | Sarubbi et al. |
| 5,804,212 | A | 9/1998 | Illum |
| 6,613,308 | B2 | 9/2003 | Bartus et al. |
| 6,737,514 | B1 | 5/2004 | Wang et al. |
| 8,283,317 | B1 * | 10/2012 | Sung ...................... A61K 31/55 514/12.1 |
| 9,561,095 | B1 * | 2/2017 | Nguyen .................. A61L 27/52 |
| 2006/0204533 | A1 | 9/2006 | Hsu et al. |
| 2007/0053870 | A1 | 3/2007 | Giyoong et al. |
| 2010/0330368 | A1 | 12/2010 | Prud'Homme et al. |

FOREIGN PATENT DOCUMENTS

| | | | | |
|---|---|---|---|---|
| KR | 20070028953 A | 3/2007 | | |
| WO | WO-9408599 A1 * | 4/1994 | ............. | A61K 38/05 |
| WO | WO-9901498 A1 * | 1/1999 | ......... | A61K 47/4823 |
| WO | WO2008/033497 * | 3/2008 | ............... | A61K 9/00 |
| WO | WO-2016004043 A1 * | 1/2016 | ........... | A61K 31/337 |
| WO | WO 2017/027216 | 2/2017 | | |
| WO | WO 2017/075369 | 5/2017 | | |
| WO | WO 2018/085407 | 5/2018 | | |

OTHER PUBLICATIONS

Gaucher et al., "Block copolymer micelles: preparation, characterization and application in drug delivery." Journal of Controlled Release 109 (2005) 169-188 (Year: 205).*

Rizvi et al., "Applications of nanoparticle systems in drug delivery technology." Saudi Pharmaceutical Journal 26 (2018) 64-70. (Year: 2018).*

Extended European Search Report for PCT/US2019/015498. Mailed Oct. 7, 2021. 7 pages.

Takenaga et al., Microparticle resins as a potential nasal drug delivery system for insulin., J Control Release, 1998, 52:81-7.

Pagels et al., Polymeric nanoparticles and microparticles for the delivery of peptides, biologics, and soluble therapeutics., Journal of Controlled Release. 2015, 219: 519-535.

Patel et al., A novel approach for antibody nanocarriers development through hydrophobic ion-pairing complexation., Journal of Microencapsulation. 2014, 31: 542-550.

Gaudana et al., Design and evaluation of a novel nanoparticulate-based formulation encapsulating a HIP complex of lysozyme., Pharm Dev Technol 2013, 18, (3), 752-9.

Mathiowitz et al., Biologically erodable microspheres as potential oral drug delivery systems., Nature 1997, 386:410-4.

Santos et al., Continuous Production of Discrete Plasmid DNA-Polycation Nanoparticles Using Flash Nanocomplexation., Small 2016, 12, (45), 6214-6222.

Vaishya et al., Long-term delivery of protein therapeutics., Expert Opin Drug Deliv 2015, 12(3), 415-40.

Heier et al., Comparison of Aflibercept, Bevacizumab, and Ranibizumab for Treatment of Diabetic Macular Edema Extrapolation of Data to Clinical Practice., JAMA Ophthalmol 2016, 134, (1), 95-9.

(Continued)

*Primary Examiner* — Walter E Webb

(74) *Attorney, Agent, or Firm* — Casimir Jones, S.C.; J. Mitchell Jones

(57) ABSTRACT

Described are new biodegradable nanoparticle platforms for encapsulation and sustained release of protein therapeutics through a scalable and reproducible method. Specifically nanoparticles comprising a complex comprising a protein, or peptide, and a counter ion polymer are described.

8 Claims, 14 Drawing Sheets

(56)  References Cited

OTHER PUBLICATIONS

Yanik et al., Randomized, Double-Blind, Placebo-Controlled Trial of Soluble Tumor Necrosis Factor Receptor: Enbrel (Etanercept) for the Treatment of Idiopathic Pneumonia Syndrome after Allogeneic Stem Cell Transplantation: Blood and Marrow Transplant Clinical Trials Network Protocol., Biol Blood Marrow Transplant 2014, 20, (6),858-64.

Dierickx et al., The role of rituximab in adults with warm antibody autoimmune hemolytic anemia., Blood 2015, 125, (21), 3223-9.

Wells et al., Aflibercept, Bevacizumab, or Ranibizumab for Diabetic Macular Edema., Ophthalmology 2016, 123, (6), 1351-9.

Xu et al., FDA Approval Summary: Nivolumab in Advanced Renal Cell Carcinoma After Anti-Angiogenic Therapy and Exploratory Predictive Biomarker Analysis., Oncologist 2017, 22, (3), 311-317.

Reck et al., Pembrolizumab versus Chemotherapy for PD-L1-Positive Non-Small-Cell Lung Cancer., N Engl J Med 2016, 375, (19), 1823-1833.

Schweizer et al., Controlled release of therapeutic antibody formats., Eur J Pharm Biopharm 2014, 88, (2), 291-309.

Patel et al., Recent Advances in Protein and Peptide Drug Delivery: A Special Emphasis on Polymeric Nanoparticles, Protein Pept Lett 2014, 21, (11), 1102-20.

Amsden., Novel biodegradable polymers for local growth factor delivery., B. Eur J Pharm Biopharm 2015, 97, (Pt B), 318-28.

Langer et al., Polymers for the sustained release of proteins and other macromolecules., Nature 1976, 263, (5580), 797-800.

Reddy et al., Exploiting lymphatic transport and complement activation in nanoparticle vaccines., Nat Biotechnol 2007, 25, (10), 1159-64.

Meyer et al., Hydrophobic Ion Pairing: Altering the Solubility Properties of Biomolecules., Pharm Res 1998, 15, (2), 188-93.

Kim et al., In situ facile-forming PEG cross-linked albumin hydrogels loaded with an apoptotic TRAIL protein., J Control Release 2015, 214, 30-9.

Byeon et al., Four-arm PEG cross-linked hyaluronic acid hydrogels containing PEGylated apoptotic TRAIL protein for treating pancreatic cancer., Acta Biomater 2014, 10, (1), 142-50.

Hulsart-Billstrom et al., Bisphosphonate-linked hyaluronic acid hydrogel sequesters and enzymatically releases active bone morphogenetic protein-2 for induction of osteogenic differentiation., Biomacromolecules 2013, 14, (9), 3055-63.

Xu et al., Hyaluronidase-incorporated hyaluronic acid-tyramine hydrogels for the sustained release of trastuzumab., J Control Release 2015, 216, 47-55.

Bae et al., Microstructured dextran hydrogels for burst-free sustained release of PEGylated protein drugs., Biomaterials 2015, 63, 146-57.

Pacelli et al., New biodegradable dextran-based hydrogels for protein delivery: Synthesis and characterization., Carbohydr Polym 2015, 126, 208-14.

Zhao et al., Multifunctional interpenetrating polymer network hydrogels based on methacrylated alginate for the delivery of small molecule drugs and sustained release of protein., Biomacromolecules 2014, 15, (9), 3246-52.

Kimura et al., Gelatin hydrogel as a carrier of recombinant human fibroblast growth factor-2 during rat mandibular distraction., J Oral Maxillofac Surg 2014, 72, (10), 2015-31.

Vermonden et al., Hydrogels for protein delivery., Chem Rev 2012, 112, (5), 2853-88.

Censi et al., Hydrogels for protein delivery in tissue engineering., J Control Release 2012, 161, (2), 680-92.

Koetting et al., pH-responsive and enzymatically-responsive hydrogel microparticles for the oral delivery of therapeutic proteins: Effects of protein size, crosslinking density, and hydrogel degradation on protein delivery., J Control Release 2016, 221, 18-25.

Peng et al., Synthesis of poly(glutamic acid)-tyramine hydrogel by enzyme-mediated gelation for controlled release of proteins., J Biomater Sci Polym Ed 2015, 26, (2), 111-27.

Bae et al., Controlled release of bone morphogenetic protein (BMP)-2 from nanocomplex incorporated on hydroxyapatite-formed titanium surface., J Control Release 2012, 160, (3), 676-84.

Peng et al., Injectable and biodegradable thermosensitive hydrogels loaded with PHBHHx nanoparticles for the sustained and controlled release of insulin., Acta Biomater 2013, 9, (2), 5063-9.

Beierle et al., Polymer nanoparticle hydrogels with autonomous affinity switching for the protection of proteins from thermal stress., Angew Chem Int Ed Engl 2014, 53, (35), 9275-9.

Patel et al., Optimization of novel pentablock copolymer based composite formulation for sustained delivery of peptide/protein in the treatment of ocular diseases., J Microencapsul 2016, 33, (2), 103-13.

Danhier et al., PLGA-based nanoparticles: an overview of biomedical applications., J Control Release 2012, 161, (2), 505-22.

Gdowski et al., Development of biodegradable nanocarriers loaded with a monoclonal antibody., J. Int J Mol Sci 2015, 16, (2), 3990-5.

Dixit et al., Poly(lactic acid)-poly(ethylene glycol) nanoparticles provide sustained delivery of a Chlamydia trachomatis recombinant MOMP peptide and potentiate systemic adaptive immune responses in mice., Nanomedicine 2014, 10, (6), 1311-21.

Varshochian et al., The protective effect of albumin on bevacizumab activity and stability in PLGA nanoparticles intended for retinal and choroidal neovascularization treatments., Eur J Pharm Sci 2013, 50, (3-4), 341-52.

Cleland et al., Development of poly-(d,I-lactide-coglycolide) microsphere formulations containing recombinant human vascular endothelial growth factor to promote local angiogenesis., J Control Release 2001, 72, (1-3), 13-24.

Chow et al., Development of highly stabilized curcumin nanoparticles by flash nanoprecipitation and lyophilization., Eur J Pharm Biopharm 2015, 94, 436-49.

Tang et al., Biodistribution and fate of core-labeled 125I polymeric nanocarriers prepared by Flash NanoPrecipitation (FNP)., J. Mater. Chem. B, 2016, 4, 2428.

Ling et al., Development of novel self-assembled DS-PLGA hybrid nanoparticles for improving oral bioavailability of vincristine sulfate by P-gp inhibition. J Control Release. Dec. 1, 2010;148(2):241-8.

Sadat et al., Improved drug loading and antibacterial activity of minocycline-loaded PLGA nanoparticles prepared by solid/oil/water ion pairing method. Int J Nanomedicine. 2012;7:221-34.

Zhou, T., "PEG-b-PCL polymeric nano-micelle inhibits vascular angiogenesis by activating p53-dependent apoptosis in zebrafish" International Journal of Nanomedicine 2016:11 6517-6531.

Hanwright et al., Sustained IGF-1 delivery ameliorates effects of chronic denervation and improves functional recovery after peripheral nerve injury and repair. Biomaterials. Jan. 2022, 280:121244.

* cited by examiner

FIGURE 2

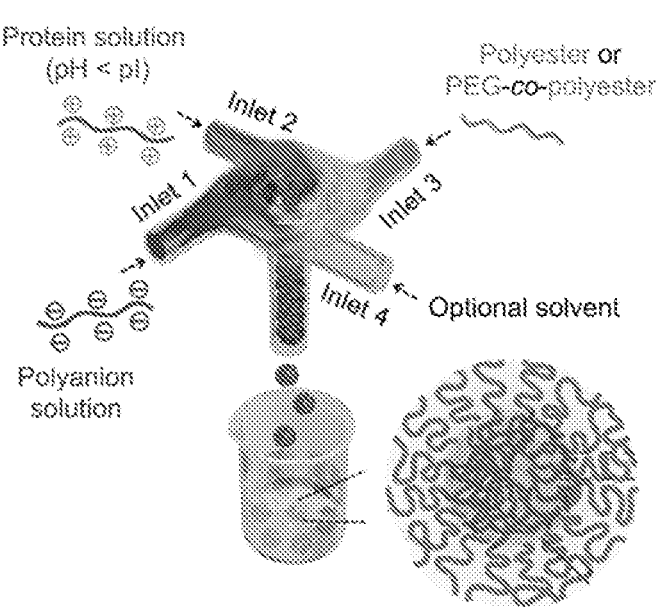

Protein solution
(pH < pI)

Inlet 2

Inlet 1

Polyester or
PEG-co-polyester

Inlet 3

Inlet 4   Optional solvent

Polyanion
solution

 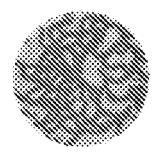

or

- PEC co-precipitates with biodegradable
  polyester nanoparticle, and distributes
  throughout the polymer nanoparticles
  or micelle core;
- Tunable size with an average of 30 nm
  to 1000 nm and a PDI < 0.3;
- Protein loading level ranging from 2 to
  25 w/w%;
- Sustained release of protein therapeutic
  over a period of 2 weeks to 3 months.

POLYMERIC NANOPARTICLE COMPOSITIONS FOR ENCAPSULATION AND SUSTAINED RELEASE OF PROTEIN THERAPEUTICS

CROSS-REFERENCE TO RELATED APPLICATIONS

This application is a 35 U.S.C. § 371 U.S. national entry of International Application PCT/US2019/015498, having an international filing date of Jan. 29, 2019, which claims the benefit of U.S. Provisional Application No. 62/623,018, filed Jan. 29, 2018, the content of each of the aforementioned applications is herein incorporated by reference in their entirety.

BACKGROUND OF THE INVENTION

Protein therapeutics are an increasingly prevalent therapeutic modality. Monoclonal antibodies, receptor traps, growth factors, and designer proteins have become important treatments for autoimmune conditions, cancer, and ophthalmologic conditions among others. Protein drugs like Avastin, Enbrel, Rituximab, Lucentis, Eylea, Optivo, Keytruda, and others account for billions dollars in annual sales. These drugs represent a large and increasing share of pharmaceutical pipelines. The specificity of action and relative paucity of off-target effects make these drugs especially attractive. Despite the growing importance of these modalities, delivery vehicles for proteins that enable spatiotemporally controlled dosing profiles are not readily available.

For delivery of protein therapeutics including antibodies, the ideal characteristics for a successful delivery system include biodegradability, high loading capacity, controlled or sustained long-term release, maintaining high stability of the protein therapeutics, and scalable production process. The high loading level is desirable since it would decrease the dosage of the delivery materials while achieving the same therapeutic effect, as most of these materials may cause side effects to healthy tissues at high concentrations in vivo. Thus, biodegradable materials are also preferable to reduce the toxicity and avoid the surgery process after cargo releasing to clear these materials out of body. Due to the low stabilities of protein therapeutics in vivo, a sustained long-term release is required for the delivery systems to maintain the therapeutic concentration in the body for a prolonged period of time, which would reduce the frequency of administration. In addition, the formulation and preparation process should maintain biological activities of the protein therapeutics. Lastly, a scalable and convenient production method is crucial for reliable manufacture and clinical translation of such a delivery system. For example, Nutropin Depot, a long-term human growth hormone somatropin-loaded injectable polymeric depot, has been removed from the market by Genentech and Alkermes in 2004, owning to the high cost in manufacturing.

Tremendous progress has been made in developing protein delivery systems to meet the key requirements mentioned above. However, the biophysical nature of protein therapeutics (i.e. high water solubility, large molecular weight, and residual surface charges) makes it more challenging to encapsulate them in a sustained release device. The most commonly studied delivery systems for protein therapeutics include hydrogels and solid polymeric nano- or microparticles. Various preparation methods have been developed for formulation optimization. Although promising results have been shown when using these systems and preparation methods for the delivery of protein therapeutics, few of them could satisfy all the above-mentioned requirements at the same time.

Hydrogel systems prepared from hydrophilic polymers, such as polyethylene glycol (PEG), hyaluronic acid, dextran, alginate and gelatin, are an appealing platform for protein delivery due to their hydrophilic nature and facile protein loading process, which avoids the denaturation of loaded protein therapeutic cargoes. In order to achieve a sustained release profile, cross-linking is required to form the network, and crosslinks could be achieved through covalent bonding, ionic or hydrophobic interactions. The release rate of a protein therapeutic from the hydrogel is controlled by the mesh size and the polymer volume fraction in the hydrogel as well as the size of loaded protein therapeutic molecules. Generally, hydrogels with smaller mesh size, higher polymer volume fraction, and larger loaded protein therapeutics would yield a slower release. The limitation of hydrogel systems is that sustained long-term release is difficult to achieve, due to the hydrophilic nature of the delivery materials used.

Another widely used carrier system for protein delivery is nano-/micro-particles prepared by hydrophobic or amphiphilic polymers. Poly(lactic acid) (PLA), poly(glycolic acid) (PGA), and their copolymers, poly(lactic-co-glycolic acid) (PLGA) are among the most extensively used polymers for particle preparation due to their biocompatibility and tunable biodegradability. The most commonly used method for encapsulating proteins into nano-/microparticles is the double emulsion method where a water/oil/water (w/o/w) emulsion system is formed; the oil phase is a solution of the carrier polymer dissolved in a water-immiscible organic solvent, the first water phase is an aqueous solution of protein therapeutic, and the second water phase is an aqueous solution as a dispersion phase. In some rare cases, a solid-in-oil-in-water (s/o/w) system is formed instead, whereas the first aqueous phase is replaced with a solid protein particles dispersed in the polymer solution in organic solvent. In both cases, the double emulsion system is kept stable while the organic solvent is gradually evaporated or extracted, generating solid polymer particles entrapping the protein solution inside. Compared with hydrogel, this system has the advantage of extending release duration since the diffusion of protein through the hydrophobic materials is negligible, and therefore release rate of the encapsulated protein therapeutics is largely dependent on the degradation rate of the polymer matrix. However, this process typically yields low loading level. In addition, the organic solvent used in this process and the hydrophobic environment in polymer matrix increase the risk of denaturation of loaded protein therapeutics. The characteristic release of the loaded protein from these particles follows three phases: burst release, dormancy, and a continuous release phase with a variable kinetics. Such a release profile makes it difficult to control the therapeutic outcomes in vivo.

Recently, the Prud'homme group developed a method for preparation of protein-loaded nanoparticles using the flash nanoprecipitation (FNP) process to enhance the loading level [1]. FNP uses a kinetic controlled process to generate nanoparticles in a continuous and scalable manner by using confined impinging jet (CIJ) or multi-inlet vortex mixer (MIVM) device, and has been used to effectively generate nanoparticles for encapsulation of small molecular weight, hydrophobic drugs. Using a modified FNP process, protein therapeutic and amphiphilic copolymer were together dissolved in a water-miscible organic solvent such as DMSO or methanol, and then rapidly mixed with a less polar nonsolvent such as chloroform or acetone in a CIJ or MIVM device to form inverse-phase (i.e. a hydrophilic core with an hydrophobic shell) nanoparticles with protein and hydrophilic segment of the copolymer in the core and the hydrophobic segment of the copolymer on the shell. The nanoparticles were then stabilized through shell cross-linking. For example, using poly(n-butylacrylate)$_{7.5kDa}$-b-poly(acrylic acid)$_{5.5kDa}$, they have successfully loaded lysozyme (14.3 kDa) as a model protein into nanoparticles (<100 nm) with high loading level (>50%). However, it is unclear whether there is a change in the secondary structure of the encapsulated protein following this nanoparticle assembly process; and more importantly, the release profile of the encapsulated protein from this system remains to be characterized.

Hydrophobic ion pairing (HIP) has been reported as a method for protein encapsulation. Through polyelectrolyte complexation, proteins with net positive charges are neutralized through complexation with oppositely charged agents such as dextran sulfate to form complex nanoparticles, which provides the protection effect to the protein as well as facilitates the encapsulation into nanoparticles. The HIP complexes were loaded into nanoparticles prepared using hydrophobic or amphiphilic polymers through the nanoprecipitation or the double emulsion method. Mitra et al. reported successful complexation of lysozyme with dextran sulfate HIP complexes, which were then loaded into PLGA nanoparticles to achieve near zero-order release kinetics over 30 days. In another study, the same group loaded IgG-Fab fragment complexed with dextran sulfate into PLGA nanoparticles through nanoprecipitation or double emulsion method with a high encapsulation efficiency of around 85% [2]. These HIP complexes and nanoparticles were prepared using manual mixing processes, with limited scalability and higher batch-to-batch variability. Consequently, a new biodegradable nanoparticle platform for encapsulation and sustained release of protein therapeutics through a scalable and reproducible method is commercially desired.

SUMMARY OF THE INVENTION

The present invention is new biodegradable nanoparticle platforms for encapsulation and sustained release of protein therapeutics through a scalable and reproducible method. Lysozyme (14.3 kDa, pI 11.3), ovalbumin (45 kDa, pI 4.5) and IgG (150 kDa, pI 6.8) were employed as models for protein therapeutics. There are two different approaches to prepare these nanoparticle platforms. In one embodiment, polyelectrolyte complexes (PEC) of lysozyme or IgG with dextran sulfate were generated through a continuous process termed flash nanocomplexation (FNC), and then co-precipitated with block copolymers such as PEG-PLLA or PEG-PCL in a solvent exchange process called flash nanoprecipitation (FNP). In a separate embodiment, the two processes of PEC complexation (FNC) and polymer nanoparticle formation as a result of flash nanoprecipitation (FNP) is combined in a single-step phase separation process. In this process, polycation solution (typically the protein solution where the solution pH is adjusted to below pI), polyanion solution (e.g. dextran sulfate, heparin sulfate, or nucleic acid), and block copolymer dissolved in a water miscible solvent (the solvent pairs are selected to properly induce phase separate at an appropriate rate) are introduced into a defined chamber at an optimized set of flow rates to achieve efficient mixing, therefore obtaining solid or micellar nanoparticles with efficient loading of PEC. It has never been reported previously that polyelectrolyte complexation and solvent-induced phase separation or self-assembly can be achieved simultaneously, such that nanoparticles (when polyester is used) or micelles (when PEG-co-polyester block copolymer is used) with PEC (e.g. protein and DS) and hydrophobic polymer co-precipitated and mixed uniformly, thus achieving sustained release of protein from the nanoparticles.

Despite of the similarity of the mixing process and mixing chamber geometry, our nanoparticle formulation is distinctive from those prepared by Prud'homme et al. in terms of the structure and composition of the nanoparticles. Our nanoparticles are composed of monolithic matrix with protein distributed throughout the nanoparticle, whereas the reverse micelles prepared by Prud'homme et al. [1] packaged protein in the hydrophilic PEG core of the micelle surrounded by a hydrophobic polymer shell. The composition of our nanoparticle includes a PEC of a protein and a polyanion (when the pH of protein solution is lower than its pI) or a polycation (when the pH of the protein solution is higher than its pI) and a hydrophobic polymer or a PEG-b-polymer block copolymer. The hydrophobic polymer does not need to contain a hydrophilic block. The micelle of Prud'homme et al. [1] does not include PEC, i.e. a counter ion polyelectrolyte.

Even though the original materials used for protein encapsulation is similar between our nanoparticles and those prepared by Mitra et al. [2], our invention describes a new process of nanoparticle preparation, which results in a new formulation of nanoparticles enables a wider range of encapsulation capacity (loading level, and types of protein and PEC). Using our processes, we encapsulate discrete PEC nanoparticles in the hydrophobic polymer nanoparticle, where PEC serves as a nucleus co-precipitated with a hydrophobic polymer, resulting in a structure of a multi-core matrix nanoparticle with PECs uniformly distributed throughout the core). More specifically, in the single-step process, the PEC forms instantaneously and serves as the nucleus to induce co-precipitation of hydrophobic polymer solid nanoparticle or micelle, yielding uniform distribution of the PEC throughout the nanoparticle. It also enables a wider range of PEC encapsulation.

One embodiment of the invention is a nanoparticle comprising: a complex comprising a protein, or peptide, and a counter ion polymer wherein the counter ion polymer has a charge enabling it to bind electrostatically to the protein. A suitable size of the nanoparticle is in the range of 20 to 2000 nm; 100 to 1800 nm; 500 to 1000 nm; 20 to 1000 nm; 20 to 500 nm; 20 to 150 nm; as examples. An example of a protein or peptide used in the present invention may have a molecular weight in the range of 2,000 to 200,000; 10,000 to 150,000; 20,000 to 100,000; 30,000 to 70,000; 2,000 to 100,000; or 100,000 to 200,000. The nanoparticle also includes a matrix comprising the complex uniformly distributed throughout a biodegradable polymer. A suitable matrix may be non-water soluble (or hydrophobic). Suitable counter ion polymers may be positively and/or negatively charged. Examples of suitable counter ion polymers include dextran sulfate (DS), heparin (heparin sulfate), hyaluronic acid, or a combination thereof. Most proteins may be used in the present invention including polypeptides and antibodies, as examples. Examples of suitable biodegradable polymers used in the present invention include a copolymer comprising PEG. Examples of copolymers include PLLA, PGA, PLGA, PCL, their PEGylated block copolymers, or a combination thereof. One suitable biodegradable polymer used in the present invention is PEG-b-PLLA.

Another embodiment of the present invention is a method of making nanoparticles comprising: (a) forming polyelectrolyte complex by mixing a protein and a counter ion polymer using a first continuous mixing process; (b) co-precipitating with a biodegradable polymer using a second continuous mixing process; and (c) forming a nanoparticle comprising the protein-polyelectrolyte complex uniformly distributed throughout the biodegradable polymer matrix. Surprisingly, the inventors discovered a one-step method of making nanoparticles of the present invention whereby nanoparticles may be formed by simultaneously performing steps (a) and (b) and the first and the second continuous process is preferably flash nanocomplexation (FNC). Specifically, the one step process preferably mixes polyelectrolyte complexes (PECs) and biodegradable polymer by solvent-induced flash nanoprecipitation (FNP). The methods of the present invention form polyelectrolyte complexes (PECs) by electrostatic attraction between the protein and the counter ion polymer. Nanoparticles are formed by the precipitation of the biodegradable polymer together with the polyelectrolyte complex (PEC).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "antibody," as used in this disclosure, refers to an immunoglobulin or a fragment or a derivative thereof, and encompasses any polypeptide comprising an antigen-binding site, regardless of whether it is produced in vitro or in vivo. The term includes, but is not limited to, polyclonal, monoclonal, monospecific, polyspecific, non-specific, humanized, single-chain, chimeric, synthetic, recombinant, hybrid, mutated, and grafted antibodies. Unless otherwise modified by the term "intact," as in "intact antibodies," for the purposes of this disclosure, the term "antibody" also includes antibody fragments such as Fab, F(ab')$_2$, Fv, scFv, Fd, dAb, and other antibody fragments that retain antigen-binding function, i.e., the ability to bind, for example, PD-L1, specifically. Typically, such fragments would comprise an antigen-binding domain.

The terms "antigen-binding domain," "antigen-binding fragment," and "binding fragment" refer to a part of an antibody molecule that comprises amino acids responsible for the specific binding between the antibody and the antigen. In instances, where an antigen is large, the antigen-binding domain may only bind to a part of the antigen. A portion of the antigen molecule that is responsible for specific interactions with the antigen-binding domain is referred to as "epitope" or "antigenic determinant." An antigen-binding domain typically comprises an antibody light chain variable region ($V_L$) and an antibody heavy chain variable region ($V_H$), however, it does not necessarily have to comprise both. For example, a so-called Fd antibody fragment consists only of a $V_H$ domain, but still retains some antigen-binding function of the intact antibody.

Binding fragments of an antibody are produced by recombinant DNA techniques, or by enzymatic or chemical cleavage of intact antibodies. Binding fragments include Fab, Fab', F(ab')2, Fv, and single-chain antibodies. An antibody other than a "bispecific" or "bifunctional" antibody is understood to have each of its binding sites identical. Digestion of antibodies with the enzyme, papain, results in two identical antigen-binding fragments, known also as "Fab" fragments, and a "Fc" fragment, having no antigen-binding activity but having the ability to crystallize. Digestion of antibodies with the enzyme, pepsin, results in a F(ab')2 fragment in which the two arms of the antibody molecule remain linked and comprise two-antigen binding sites. The F(ab')2 fragment has the ability to crosslink antigen. "Fv" when used herein refers to the minimum fragment of an antibody that retains both antigen-recognition and antigen-binding sites. "Fab" when used herein refers to a fragment of an antibody that comprises the constant domain of the light chain and the CHI domain of the heavy chain.

By "counter ion polymer" is meant a polymer having a charge so that the polymer is able to bind electrostatically to a protein. Examples include a protein that is net positively charged the binds to a counter ion polymer that has a net negative charge or vice versa.

By "disease" is meant any condition or disorder that damages or interferes with the normal function of a cell, tissue, or organ. An example of a disease includes cancer.

By "fragment" is meant a portion of a polypeptide. This portion contains, preferably, at least 10%, 20%, 30%, 40%, 50%, 60%, 70%, 80%, or 90% of the entire length of the reference polypeptide. A fragment may contain 10, 20, 30, 40, 50, 60, 70, 80, 90, or 100, 200, 300, 400, 500, 600, 700, 800, 900, or 1000 amino acids.

The term "mAb" refers to monoclonal antibody. Antibodies of the invention comprise without limitation whole native antibodies, bispecific antibodies; chimeric antibodies; Fab, Fab', single chain V region fragments (scFv), fusion polypeptides, and unconventional antibodies.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

A "reference sequence" is a defined sequence used as a basis for sequence comparison. A reference sequence may be a subset of or the entirety of a specified sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids.

As used herein, the term "subject" is intended to refer to any individual or patient to which the method described herein is performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Any compositions or methods provided herein can be combined with one or more of any of the other compositions and methods provided herein.

BRIEF DESCRIPTION OF THE DRAWINGS

FIG. 2. Schematic illustration of single-step encapsulation of protein therapeutics using a four-inlet multi-inlet vortex mixer. PEC co-precipitates with biodegradable polyester nanoparticles, and distributes throughout the polymer nanoparticles or micelle core. Tunable size with an average of 30 nm to 1000 nm and a PDI<0.3. Protein loading level ranging from 2 to 25%. Sustained release of protein therapeutic over a period of 2 weeks to 3 weeks.

8 ticles with DS only, and lysozyme/DS PEC nanoparticles without mPEG-PCL at (A) 0.5 mL/min flow rates in all four inlets and (B) at 2 mL/min (DS, lysozyme, mPEG-PCL) and 4 mL/min (water) flow rates in each of the four inlets.

Figure 9A:
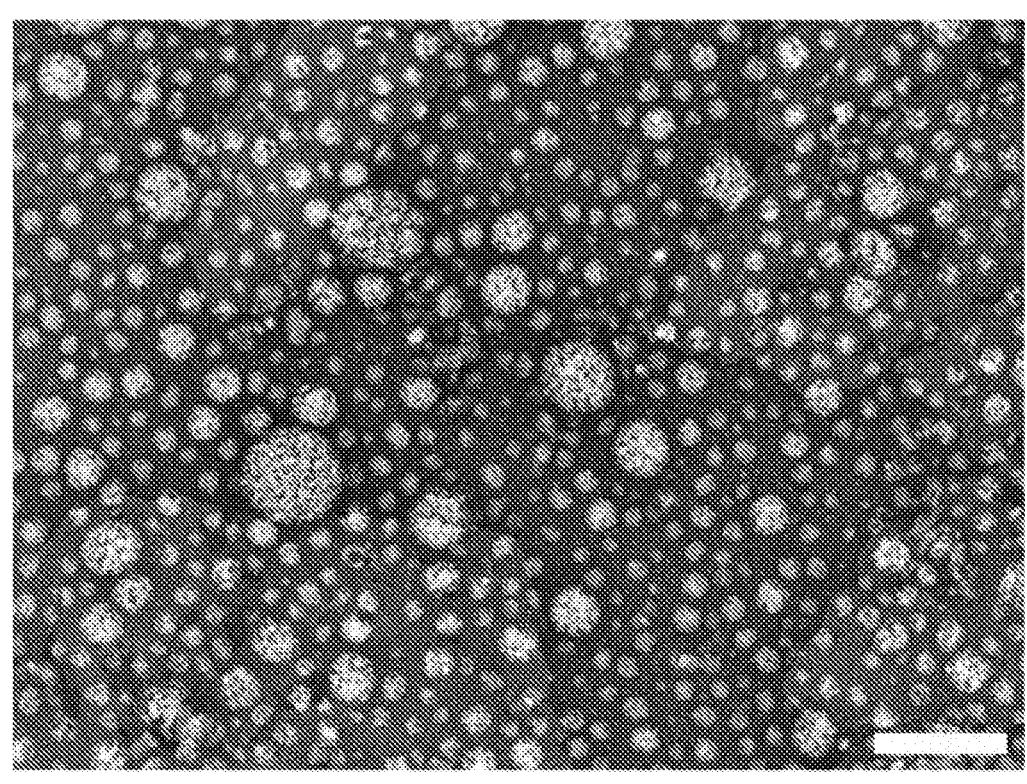
Figure 9B:
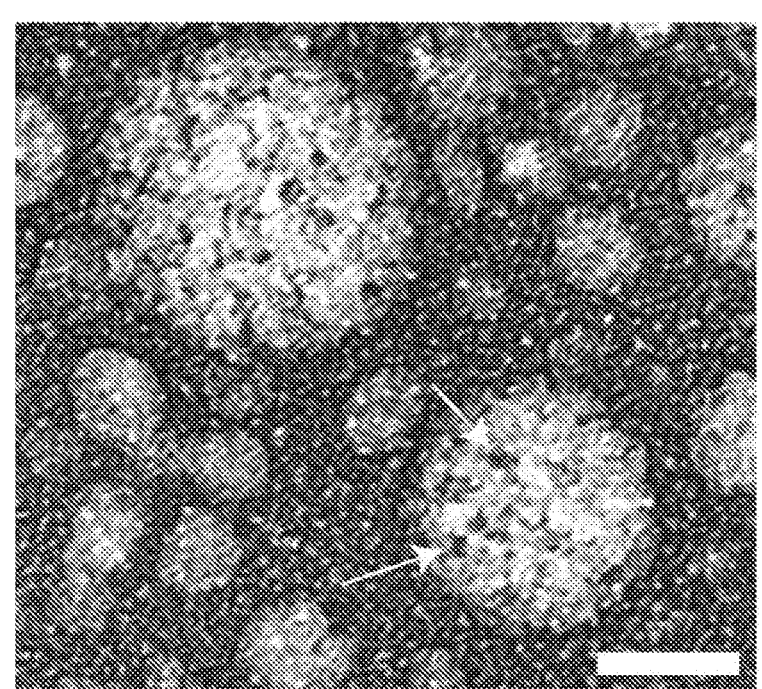

FIG. 9A-9B. (A) Transmission electron microscopy (TEM) image of mPEG-PCL nanoparticles with encapsulated NanoGold-labeled immunoglobulin G (IgG)/DS PEC. Scale bar=100 nm. (B) A higher magnification TEM indicating the distribution of IgG inside the nanoparticles. Arrows are examples of NanoGold labeled IgG. Scale bar=50 nm.

Figure 10A:
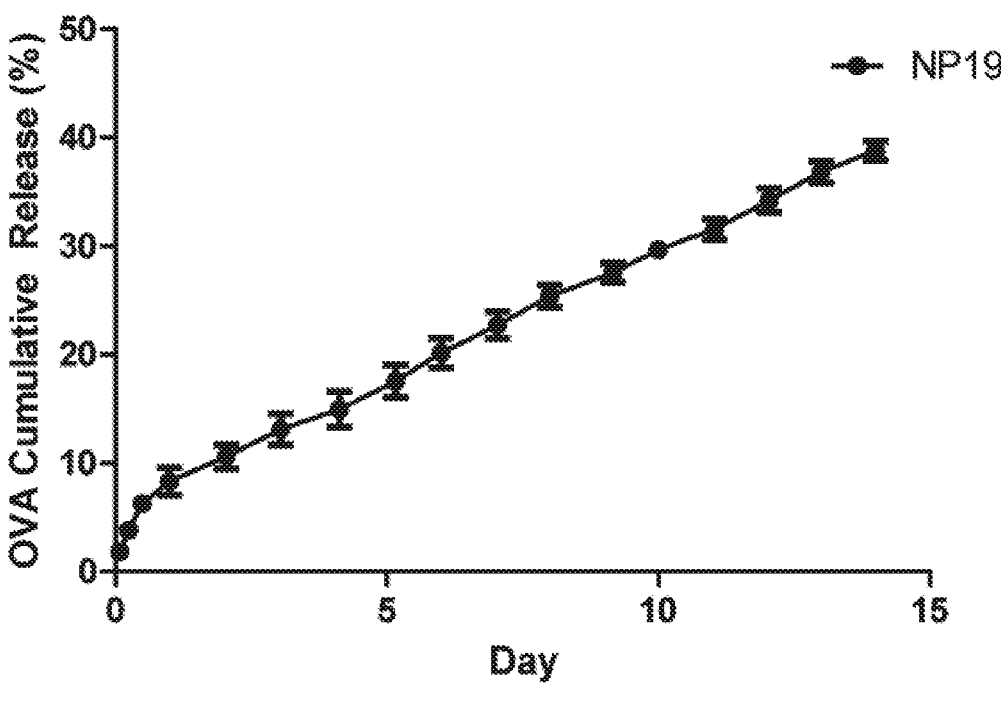
Figure 10B:
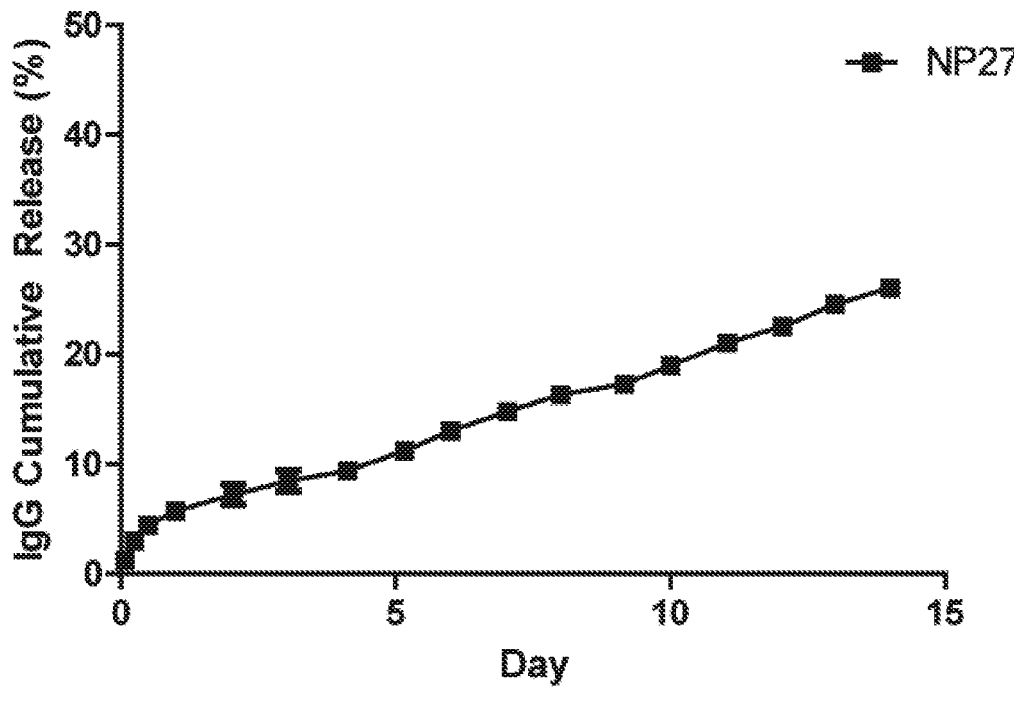

FIG. 10A-10B. In vitro release profiles of protein therapeutics from protein/DS:mPEG-PCL nanoparticles over a two-week period in PBS (pH 7.4) at 37° C., (A) using IgG as a model protein releasing from NP19 and (B) using ovalbumin (OVA) as a model protein releasing from NP27.

DETAILED DESCRIPTION OF THE INVENTION

Figure 1:
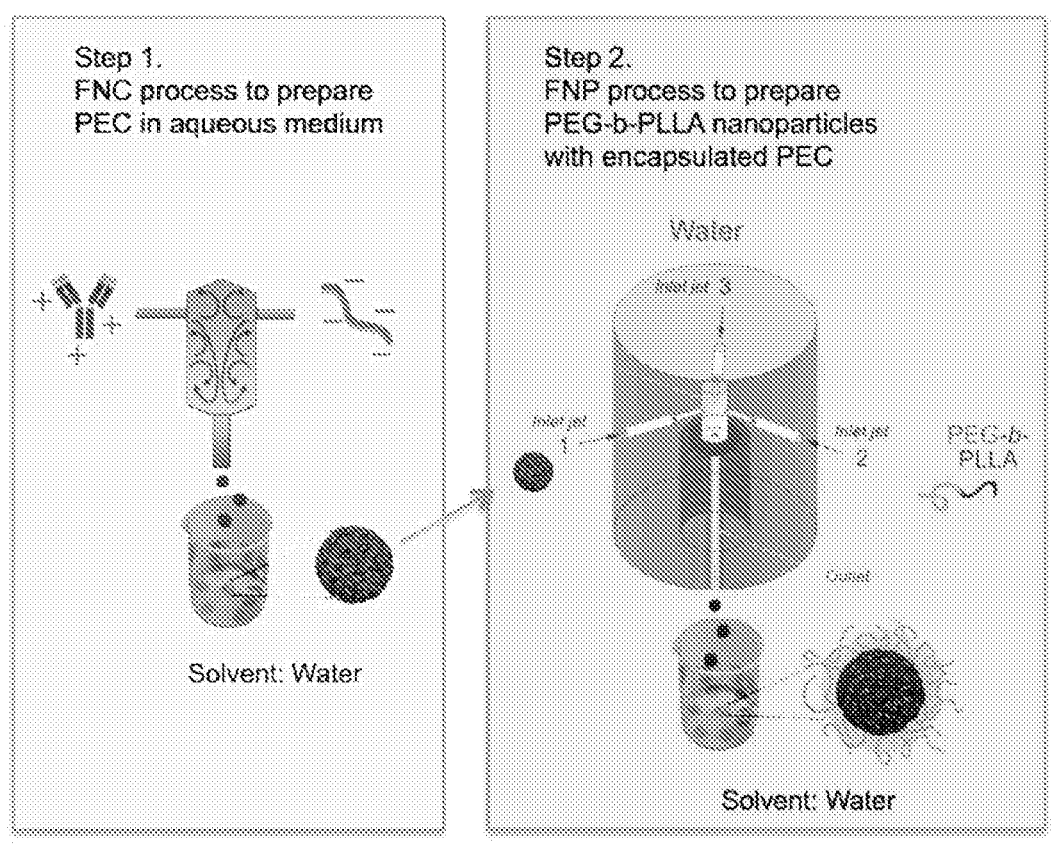
FIG. 1. Schematic illustration of the two-step (FNC-FNP) preparation process of nanoparticles with encapsulated PEC of a protein therapeutic and a counter ion polyelectrolyte. A three-inlet device is shown here for the second step. It is possible to switch this to a two-inlet or a four-inlet mixing chamber based on the specific requirements for solvent exchange in the FNP process.

The present invention includes methods to preparing nanoparticles with encapsulated polyelectrolyte complexes (PEC) of one or more proteins and counter ion polyelectrolytes. This process is comprised of two sequential steps: (1) a selected protein therapeutic is complexed with a polyanion (e.g. dextran sulfate (DS), heparin (heparin sulfate) and hyaluronic acid etc.) at a pH that is lower than the isoelectric point (pI) of the protein, yielding PEC suspended in water or an aqueous solvent, and (2) the PEC suspension is co-precipitated with biodegradable polymer PEG-b-PLLA (or PLLA, PGA, PLGA, PCL, or their copolymers with PEG, or their combinations) dissolved in a water-miscible organic solvent (e.g. acetyl nitrile (ACN), dimethyl sulfoxide (DMSO), tetrahydrofuran (THF), dimethylformamide (DMF), and isopropyl alcohol (IPA) etc.); both steps are achieved by infusing solution jets at a set of predetermined flow rates through a confined impinging jet mixer or a multi-inlet vortex mixer. This two-step process results in the formation of PEC-containing nanoparticles (FIG. 1).

Alternatively, the nanoparticles are formed by a simultaneous polyelectrolyte complexation and flash nanoprecipitation process that is comprised of continuously infusing solution jets of: (1) a selected protein therapeutic dissolved in an aqueous solvent at a pH that is lower than the isoelectric point (pI) of the protein, (2) a polyanion, e.g. dextran sulfate (DS), heparin (heparin sulfate) and hyaluronic acid etc., dissolved in an aqueous solvent, (3) a biodegradable polymer PEG-b-PLLA (or PLLA, PGA, PLGA, PCL, or their copolymers with PEG, or their combinations) dissolved in a water-miscible organic solvent (e.g. acetyl nitrile (ACN), dimethyl sulfoxide (DMSO), tetrahydrofuran (THF), dimethylformamide (DMF), and isopropyl alcohol (IPA), etc.), and (4) additional solvent jet to maintain achieve a specific solvent polarity in order to induce efficient phase separation and nanoparticle formation, at a set of predetermined flow rates through a confined impinging jet mixer or a multi-inlet vortex mixer, resulting in the formation of PEC-containing nanoparticles (FIG. 2).

The present invention also includes nanoparticle systems that are made by the methods of the present invention. This nanoparticle system is composed of biodegradable polymer matrix embedded with protein-polyion PEC with the following characteristics: (1) PEC nanoparticles serving as the multiple nuclei co-precipitated with biodegradable polymer nanoparticle (optionally, some nanoparticles also contain a PEG corona), whereas the PECs are distributed throughout the polymer nanoparticles; (2) tunable size with an average of 30 nm to 1000 nm and polydispersity index (PDI) of 0.3 or lower; (3) protein loading level ranging from 2 to 25 w/w %; and (4) sustained release of protein therapeutics over a period ranging from 2 weeks to 3 months.

To illustrate this invention, the inventors describe examples of the preparation and characterizations of lysozyme-, ovalbumin-, and IgG-loaded PLLA nanoparticles, or PEG-b-PLLA or PEG-b-PCL micellar nanoparticles.

Example 1. Preparation of Lysozyme/DS:PEG-b-PLLA Nanoparticles

Methods

Preparation and characterization of PEC nanoparticle core: Lysozyme was dissolved in deionized (DI) water at a concentration of 5 mg/mL, followed by adjusting pH to 4.0 by adding 0.1 M HCl solution. One milliliter of the In vitro release of protein: One mL of lysozyme-loaded nanoparticle suspension containing 1 mg of lysozyme was added into a 1-mL dialysis tube (SpectrumLab, MWCO 50 kDa), which was then submerged in a vial containing 5 mL of PBS (pH 7.4). The vial was put into an incubator with an agitation rate 100 rpm at 37° C. The outside PBS medium were collected and replaced with free PBS daily. The collected medium was concentrated by lyophilization and further reconstituted in 400 microliters of DI water. Micro bicinchoninic acid (BCA) assay was employed to quantify the amount of released lysozyme.

Results and Discussion

Figure 3:
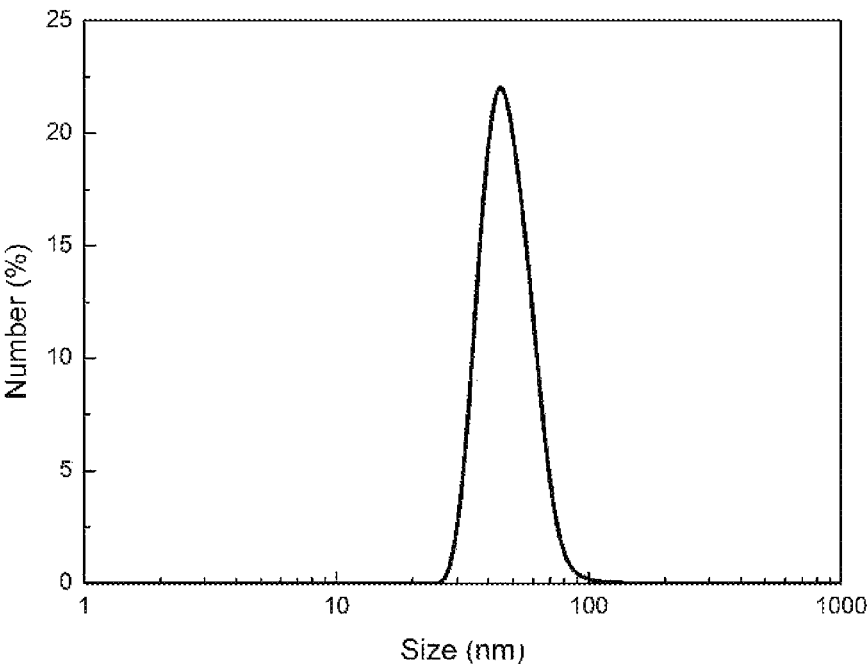
FIG. 3. Size distributions of lysozyme/DS PEC nanoparticles (A) and lysozyme/DS:PEG-b-PLLA nanoparticles (B) measured by DLS in water. Three batches of core-shell nanoparticles (NP1, NP2, and NP3) were prepared at three different lysozyme to polymer weight ratios, showing the average particle size ranging from 124 to 170 nm with a narrow size distribution (PDI 0.17-0.19) (Table 1). (C) Effect of lysozyme to polymer ratio on nanoparticle size distribution. (D) The average zeta potentials of NP1 to NP3 measured in DI water.
Figure 4:
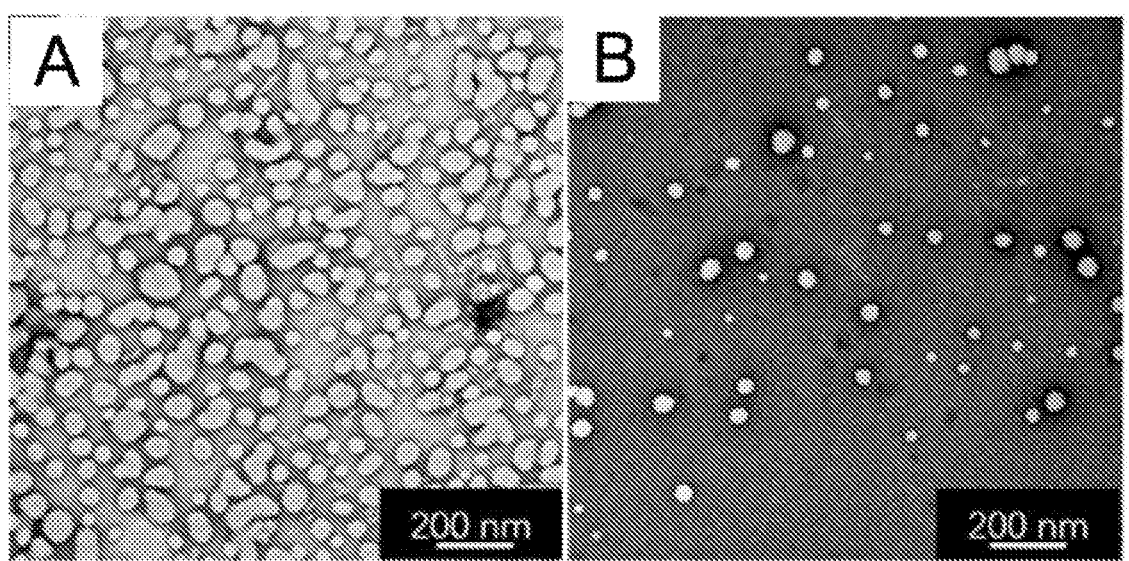
FIG. 4A-4B. TEM images of NP1 (A) and NP2 (B).

PEC nanoparticle preparation and characterization: After rapid mixing through FNC, lysozyme and DS formed uniform PEC nanoparticles in an aqueous solution with an average particle size of 64 nm and a polydispersity index (PDI) of 0.18 (FIG. 3).

TABLE 1

Summary of particle size, PDI, zeta potential, EE, and loading level of lysozyme in NP1 to NP3

| Nanaoparticle | Lysozyme to polymer ratio | Size (nm) | PDI | Zeta potential (mV) | EE (%) | LL (%) |
|---|---|---|---|---|---|---|
| NP1 | 1:3 | 123.5 ± 0.9 | 0.18 ± 0.03 | −27.2 ± 2.1 | 70.3 ± 4.1 | 14.5 ± 1.7 |
| NP2 | 1:5 | 152.2 ± 4.7 | 0.19 ± 0.02 | −26.1 ± 2.3 | 83.6 ± 3.1 | 11.8 ± 0.6 |
| NP3 | 1:10 | 169.5 ± 3.3 | 0.17 ± 0.03 | −23.6 ± 1.7 | 89.3 ± 2.7 | 8.2 ± 0.5 | lysozyme solution was then rapidly mixed with an equal volume of DS solution (20 mg/mL, pH was adjusted to 4.0) through a CIJ mixer with two inlets at a flow rate of 5 mL/min. The size of the obtained lysozyme/DS PEC nanoparticles was characterized using a dynamic light scattering (DLS) Zetasizer Nano (Malvern Instruments, Worcestershire, UK). Each sample was measured for three runs and the data was reported as the mean±standard deviation of three readings.

Preparation and characterization of PEG-b-PLLA micellar nanoparticles: One milliliter of the lysozyme/DS PEC nanoparticle suspension obtained in the previous step (2.5 mg/mL) was rapidly mixed with an equal volume of a solution of $PEG_{5k}$-b-$PLLA_{20k}$ dissolved in DMSO at various concentrations (7.5, 12.5, and 25 mg/mL) through a two-inlet CIJ mixer at a flow rate of 5 mL/min. Three nanoparticles (NP1, NP2, and NP3) with different lysozyme to polymer weight ratios (1:3, 1:5 and 1:10) were obtained. The nanoparticles were dialyzed against DI water using dialysis membrane with molecular weight cut-off (MWCO) 3.5 kDa for 12 hours to remove DMSO, with water being changed every 2 hours. The obtained solutions were purified by ultra-filtration using a filter with MWCO 100 kDa at 4,500 rpm for 20 min to remove excess protein and DS. The amount of unencapsulated lysozyme was measured by the BCA assay, and the encapsulation efficiency (EE) was calculated using the following formula: EE (%)=($M_{total}$−$M_{free}$)/$M_{total}$×100%, where $M_{total}$ represents the mass of the total feeding lysozyme and $M_{free}$ represents the mass of free lysozyme. The nanoparticles were characterized by particle size and zeta potential using a DLS Zetasizer Nano. Each sample was measured for three runs and the data was reported as the mean±standard deviation of three readings. Samples for TEM imaging were prepared by adding 10 microliters of nanoparticle solution onto an ionized nickel grid covered with a carbon film. After 10 min, the solution was pipetted away, and a 6-microliter drop of 2% uranyl acetate was added to the grid. After 30 seconds, the solution was removed, and the grid was left to dry at room temperature. The samples were then imaged using a Technai FEI-12 electron microscope.

Example 2. Preparation and Characterization of IgG-Encapsulated PEG-b-PLLA Nanoparticles Methods Preparation and characterization of IgG/DS PEC nanoparticles: IgG was dissolved in DI water at a concentration of 5 mg/mL, followed by adjusting pH to 4.0 by adding 0.1 M HCl solution. One milliliter of the IgG solution was then rapidly mixed with an equal volume of DS solution (20 mg/mL, pH was adjusted to 4.0) through a CIJ mixer with two inlets at a flow rate of 5 mL/min. The obtained PEC nanoparticle suspension was used immediately for PEG-b-PLLA nanoparticle preparation.

Figure 5:
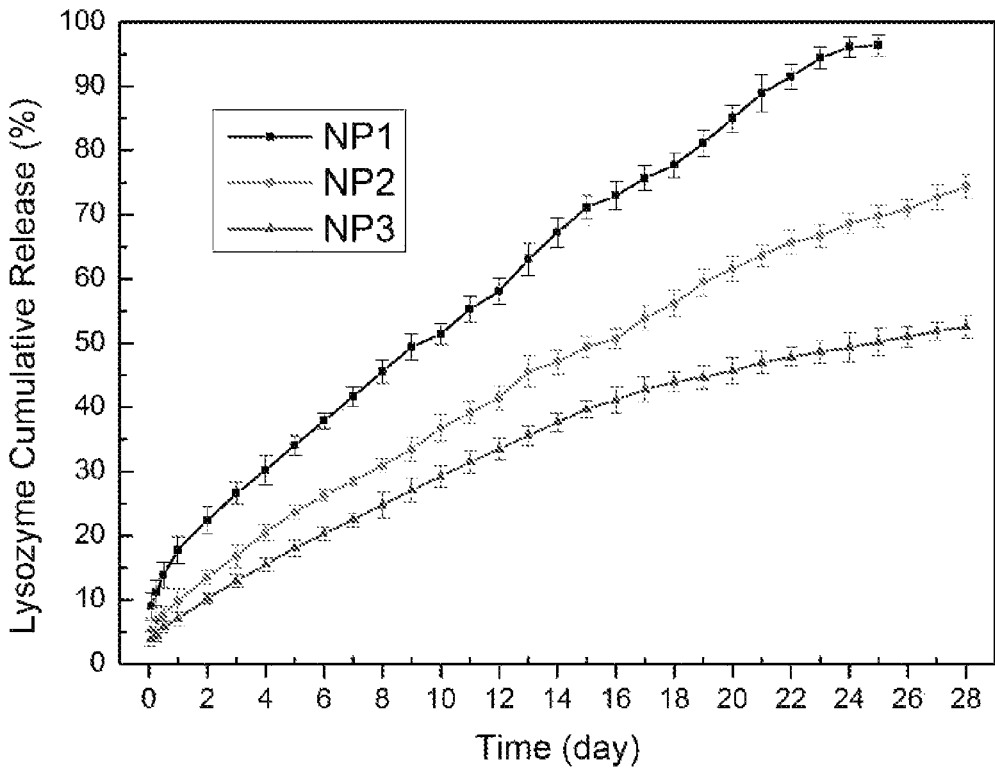
FIG. 5. In vitro release profiles of lysozyme from NP1-NP3 in PBS (pH 7.4) at 37° C.

Preparation and characterization of IgG/DS:PEG-b-PLLA nanoparticles: One mL of the IgG/DS PEC nanoparticle suspension obtained in the previous step (2.5 mg/mL) was rapidly mixed with an equal volume of $PEG_{5k}$-b-$PLLA_{20k}$ DMSO solution at two different concentrations (12.5 and 25 mg/mL) through a two-inlet CIJ mixer at a flow rate of 5 or 10 mL/min to obtained four different formulations of core-shell nanoparticles (NP4 to NP7, Table 2) with two different IgG to polymer ratios (1:5 and 1:10) (FIG. 5). The nanoparticles were dialyzed against DI water using dialysis membrane with MWCO 3.5 kDa for 12 hours to remove DMSO, with water being changed every 2 hours. The obtained solutions were purified by ultra-filtration using a filter with MWCO 100 kDa at 4,500 rpm for 20 min to remove excess IgG and DS. The amount of IgG in the filtrate was measured by micro BCA assay, and the EE was calculated using the following formula: EE (%)=($M_{total}$−$M_{free}$)/$M_{total}$×100%, where $M_{total}$ represents the mass of the total feeding IgG and $M_{free}$ represents the mass of free IgG. The core-shell nanoparticles were characterized by size and zeta potential using a DLS Zetasizer Nano. Each sample was measured for three runs and the data was reported as the mean±standard deviation of three readings.

In vitro release of IgG: One mL of IgG-loaded nanoparticle suspension containing 1 mg IgG was added into a 1-mL dialysis tube (SpectrumLab, MWCO 300 kDa), which was then submerged in a vial containing 5 mL of PBS (pH 7.4).

The vial was put into an incubator at 37° C. with an agitation rate of 100 rpm. The PBS solution in the bath was collected and refreshed daily. The collected medium was concentrated by lyophilization and further reconstituted using 400 microliters of DI water. Micro BCA assay was employed to quantify the amount of released IgG.

Results

Core-shell nanoparticle preparation and characterization: The IgG/DS:PEG-b-PLLA nanoparticles (NP4 to NP7) were prepared at two different IgG to polymer ratios and two different flow rates, showing a Z-average particle size ranging from 35 nm to 96 nm with a narrow size distribution (PDI values~0.16-0.26) (Table 2). Decreasing the ratio of IgG to polymer or the flow rate significantly increased the nanoparticle size. These results demonstrated that the particle size of the nanoparticles can be varied through tuning the weight ratio of IgG to polymer as well as the flow rate. All the nanoparticles showed negative surface charges with zeta potential ranging from −24 to −33 mV. The encapsulation efficiencies ranged from 62 to 88%, which increased with the increase of flow rate or the decrease of IgG to polymer ratio.

$PEG_{5k}$-b-$PLLA_{20k}$ was replaced with $PEG_{5k}$-b-$PCL_{20k}$. Four nanoparticles NP8-NP11 were prepared with two different IgG to polymer ratios (1:5 and 1:10) and two different flow rates (5 and 10 mL/min) (FIG. 5B).

In vitro release of IgG: One mL of IgG/DS:PEG-b-PCL nanoparticle solution containing 200 micrograms of IgG was added into a 1-mL dialysis tube (SpectrumLab, MWCO 300 kDa), which was then submerged in a vial containing 5 mL of PBS (pH 7.4). The vial was put into an incubator with an agitation rate of 100 rpm at 37° C. The PBS filtrate was collected and refreshed daily. The collected medium was concentrated by lyophilization and further reconstituted using 400 microliters of DI water. Micro BCA assay was employed to quantify the amount of released IgG.

Results

Core-shell nanoparticle preparation and characterization: NP8-NP11 showed a Z-average particle size ranging from 54 to 69 nm with a narrow size distribution (PDI values~0.13-0.22) (Table 3). In particular, we found that a

TABLE 2

Summary of average particle size, PDI, zeta potential, EE and loading levels of IgG in NP4 to NP7

| Nanoparticle | IgG to polymer ratio | Flow rate (mL/min) | Size (nm) | PDI | Zeta potential (mV) | EE (%) | LL (%) |
|---|---|---|---|---|---|---|---|
| NP4 | 1:3 | 5 | 64.1 ± 3.2 | 0.26 ± 0.01 | −26.0 ± 1.3 | 62.4 ± 3.1 | 11.8 ± 0.4 |
| NP5 | 1:10 | 5 | 62.6 ± 1.7 | 0.21 ± 0.02 | −23.6 ± 0.5 | 76.2 ± 3.3 | 7.8 ± 1.1 |
| NP6 | 1:5 | 10 | 35.4 ± 3.9 | 0.16 ± 0.03 | −32.7 ± 2.2 | 79.1 ± 2.4 | 10.9 ± 0.8 |
| NP7 | 1:10 | 10 | 96.2 ± 1.5 | 0.20 ± 0.02 | −27.4 ± 0.8 | 87.9 ± 1.4 | 7.3 ± 1.4 |

In vitro release profiles: The in vitro release profiles of NP4 to NP7 were investigated in PBS (pH 7.4) using the dialysis method. As shown in FIG. 5A, all the four nanoparticles showed similar biphasic releaser profiles with burst releases during the first two days, followed by near zero-order releases over 34 days. In addition, NP4 to NP7 showed similar release rates with about 57%, 54%, 53% and 51% decrease in the ratio of IgG to polymer or a decrease in the flow rate increased the particle size, which is consistent with the results of IgG/DS:PEG-b-PLLA nanoparticles. All the nanoparticles showed negative surface charges with zeta potential ranging from −24 to −30 mV. The EEs of NP8 to NP11 ranged from 69% to 90%, which increased with the increase of flow rate or the decrease of IgG to polymer ratio.

TABLE 3

Z-average sizes, PDIs, zeta potentials, encapsulation efficiencies, and loading levels of IgG in NP8 to NP11

| Nanoparticle | IgG to polymer ratio | Flow rate (mL/min) | Size (nm) | PDI | Zeta potential (mV) | EE (%) | LL (%) |
|---|---|---|---|---|---|---|---|
| NP8 | 1:5 | 5 | 66.0 ± 2.2 | 0.19 ± 0.02 | −26.4 ± 2.1 | 68.9 ± 2.8 | 12.1 ± 0.5 |
| NP9 | 1:10 | 5 | 68.8 ± 0.8 | 0.16 ± 0.04 | −24.7 ± 1.8 | 81.2 ± 1.4 | 7.2 ± 0.8 |
| NP10 | 1:5 | 10 | 61.2 ± 1.7 | 0.22 ± 0.01 | −29.8 ± 1.4 | 78.5 ± 2.3 | 10.3 ± 0.9 |
| NP11 | 1:10 | 10 | 54.7 ± 2.1 | 0.13 ± 0.02 | −27.2 ± 2.3 | 89.3 ± 2.4 | 7.7 ± 1.1 |

IgG released from NP4 to NP7, respectively, by day 34; and 95%, 87%, 85%, 82%, respectively, by day 76.

Example 3. Preparation of IgG/DS:PEG-b-PCL Nanoparticles

Methods

Preparation and characterization of IgG/DS:PEG-b-PCL nanoparticles: The IgG/DS:PEG-b-PCL nanoparticles were prepared and characterized using the same procedures as described in the method section in Example 2, except that In vitro release of IgG: The in vitro release profiles of IgG from NP8 to NP11 were investigated in PBS (pH 7.4) using the dialysis method. As shown in FIG. 5, all the four nanoparticles showed similar biphasic release profiles with burst releases during the first two days and followed by near zero-order releases over the next 27 days. In addition, all four nanoparticle formulations yielded similar release rates with 40-45% IgG released by day 27. These nanoparticles are expected to have longer release periods following the similar trend of release between day 4 to 27.

Figure 6A:
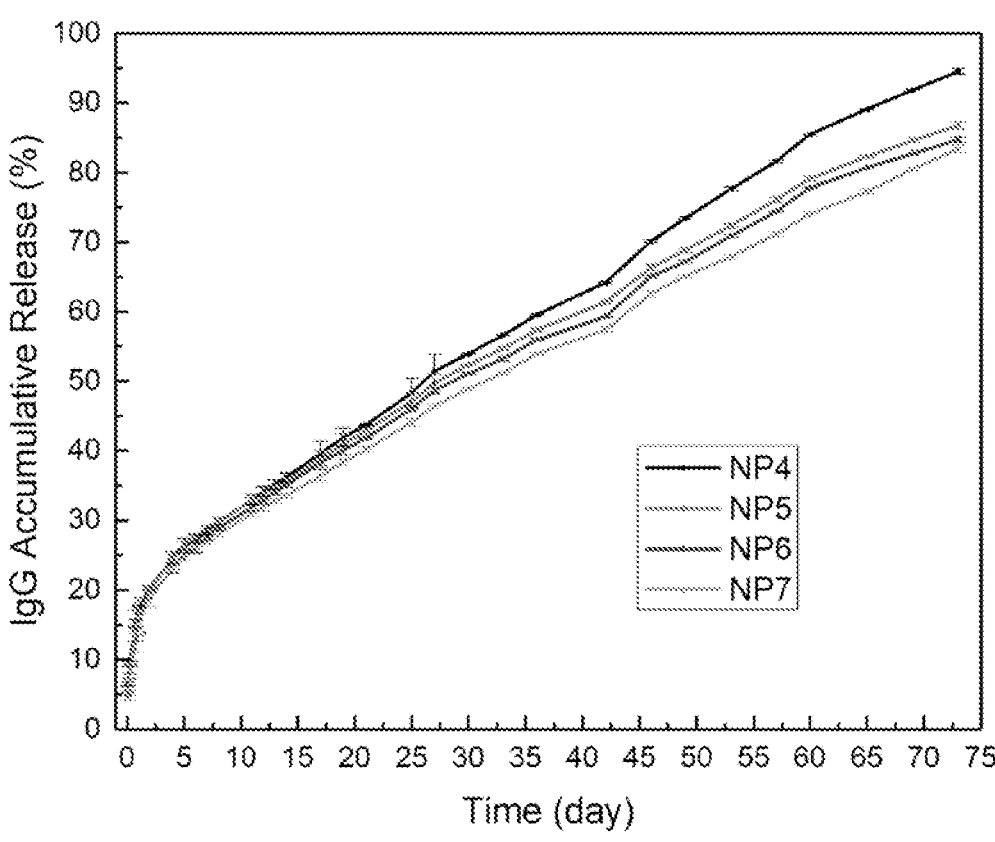
FIG. 6A-6B. (A) In vitro release profiles of IgG from NP4-NP7 in PBS (pH 7.4) at 37° C. (B) In vitro release profiles of IgG from NP8-NP11 in PBS (pH 7.4) at 37° C.
Figure 6B:
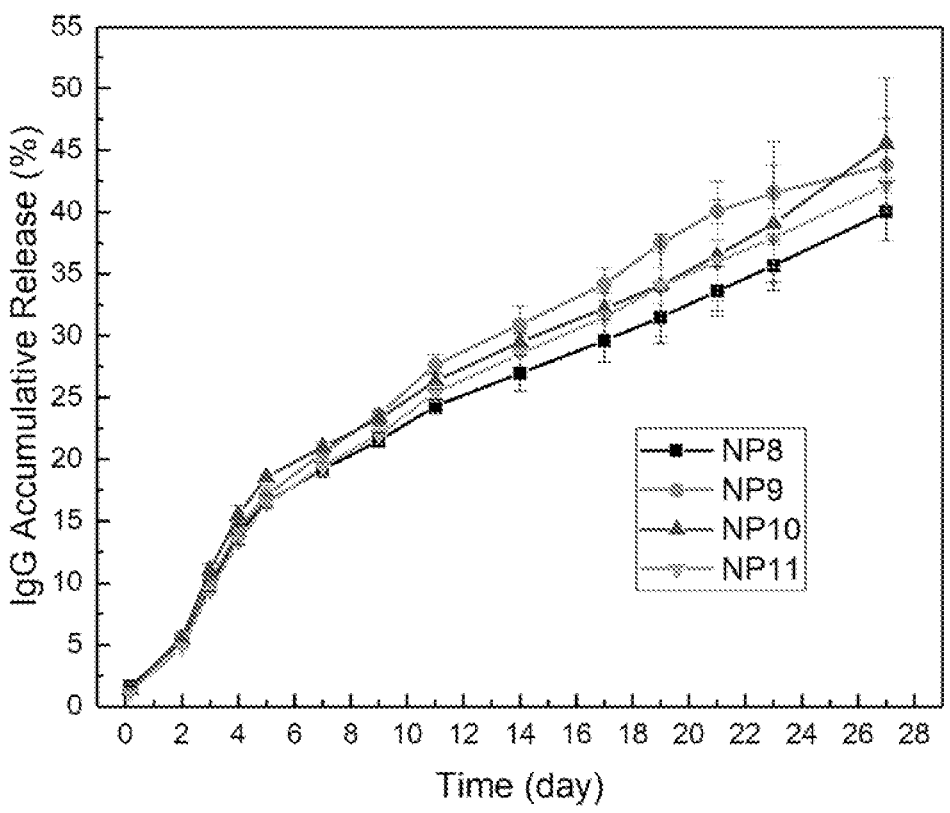
Figure 7:
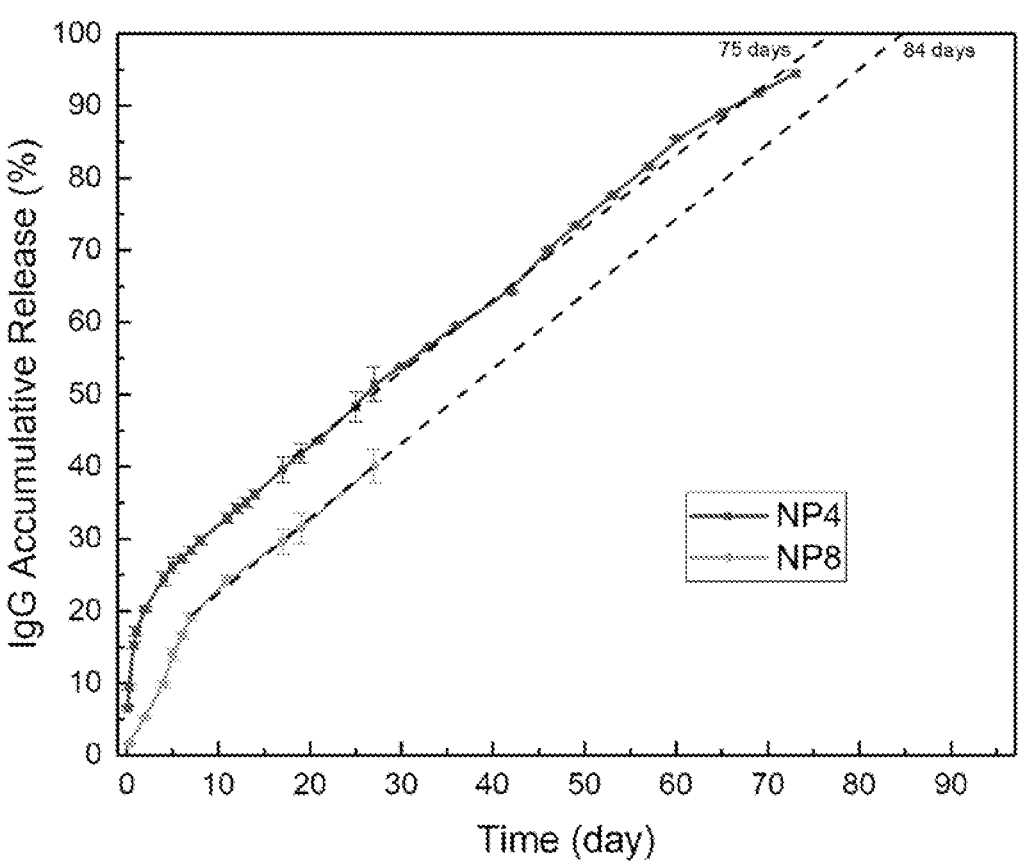
FIG. 7. Comparison of the release profiles of NP4 and NP8.
Figure 8A:
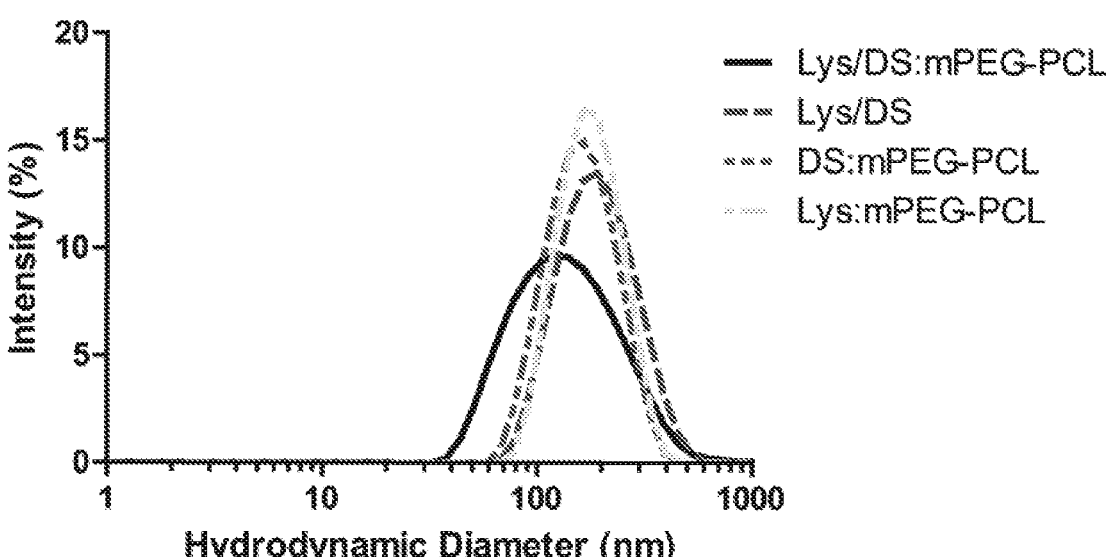
FIG. 8A-8B. Distribution of intensity average size measured in water by dynamic light scattering (DLS) for mPEG-PCL nanoparticles with encapsulated lysozyme/dextran sulfate (DS) PEC, in comparison with mPEG-PCL nanoparticles with lysozyme only, mPEG-PCL nanopar-
Figure 8B:
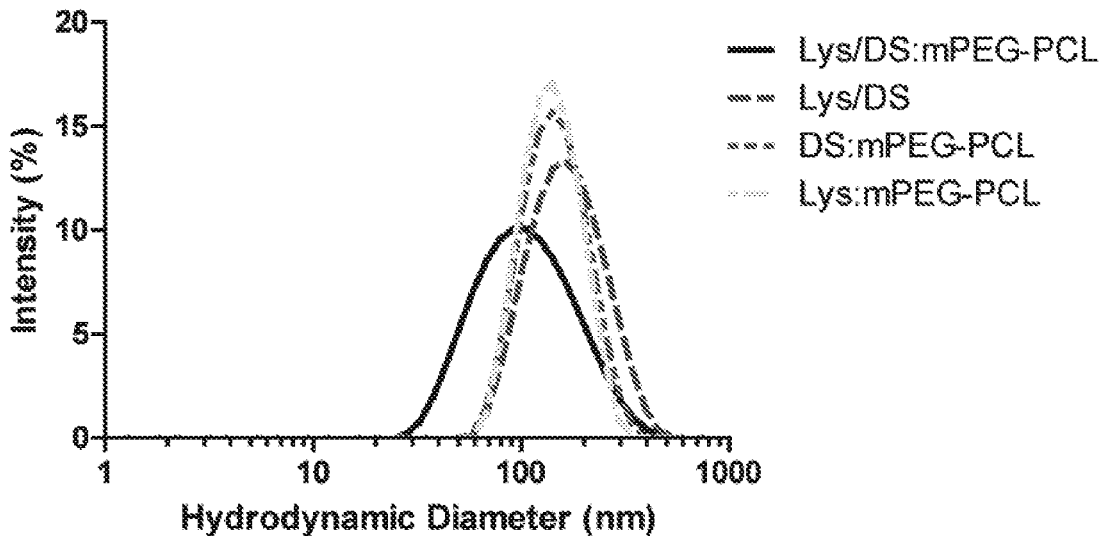

Comparison between IgG/DS:PEG-b-PLLA and IgG/DS:PEG-b-PCL nanoparticles: The release profiles of NP4 and NP8 which were prepared under the same conditions were compared in FIG. 6. It can be seen that: (1) NP4 had a burst release at the first two days with 20% IgG released, while NP8 only released 15% IgG within the first 4 days; (2) NP8 may have a longer release duration than NP8, as estimated by extrapolating the release profile (FIG. 6). These results demonstrated that the release profile of this system could be modified by choosing different polymers with different degradation rates.

Example 4. Preparation of Lysozyme/DS:mPEG-b-PCL Nanoparticles by the One-Step Method Methods Preparation and characterization of lysozyme/DS:mPEG-b-PCL nanoparticles: Lysozyme was dissolved in deionized (DI) water at a concentration of 0.5 mg/mL and its pH was tuned to 8.0 using 0.1 M NaOH. One milliliter of lysozyme (pH 8.0, 0.5 mg/mL) was mixed with equal volumes of $mPEG_{10K}$-b-$PCL_{40K}$ at various concentrations (1.5, 2.5, 5.0, 7.5 mg/mL, dissolved in DMSO), dextran sulfate (0.5 mg/mL, dissolved in DI water), and DI water (pH 7.4) through a four-inlet multi-inlet vortex mixer (MIVM) at various flow rate ratios (Table 4). The nanoparticles were dialyzed against 4 liters of DI against a dialysis membrane (MWCO 3.5 kDa) for 24 hours to remove DMSO with water nanoparticles, the missing component—DS, lysozyme, and mPEG-b-PCL, respectively—was substituted with the corresponding component's solvent alone. The nanoparticles were then prepared and characterized in the same manner as lysozyme/DS:mPEG-b-PCL nanoparticles.

Results and Discussion

Under flash mixing conditions that generate turbulent flow patterns inside the MIVM chamber, lysozyme and DS formed complexes that were then coated by mPEG-b-PCL as a result of precipitation due to solvent polarity change under the mixing condition. The lyosozyme/DS nanocomplexes served as nucleation site for mPEG-b-PCL precipitation, which ensured the rapid and uniform growth of the mPEG-b-PCL nanoparticles in a continuous and scalable manner. The weight ratio of lysozyme to DS was optimized as described in Example 1. The flow rates of mPEG-b-PCL solution, DS solution, lysozyme solution, and DI water were controlled to be 9:9:9:1. By varying the mPEG-b-PCL: lysozyme mass ratio and the flow rates of the solutions, different batches of nanoparticles with an average size of 70 to 120 nm were generated with relatively narrow distributions as measured by polydispersity index (PDI). The encapsulation of lysozyme was near completion (>97.2%) under all conditions tested in Table 4. In general, higher flow rates yielded smaller nanoparticle size.

TABLE 4

| | | | | | | | | |
|---|---|---|---|---|---|---|---|---|
| Summary of particle sizes, PDIs, zeta potentials, EEs, and LLs of NP12 to NP18 | | | | | | | | |
| Nanoparticle | Polymer to lysozyme mass ratio | Water flow rate (mL/min) | Polymer, DS, and Lysozyme flow rates (mL/min) | Size (nm) | PDI | Zeta potential (mV) | EE (%) | LL (%) |
| NP12 | 3 | 0.5 | 4.5 | 111.47 ± 0.97 | 0.18 ± 0.02 | −16.27 ± 1.18 | 98.9900% | 19.8% |
| NP13 | 3 | 5.0 | 45.0 | 77.06 ± 3.16 | 0.30 ± 0.06 | −25.27 ± 1.86 | 98.3900% | 19.7% |
| NP14 | 5 | 0.5 | 4.5 | 120.57 ± 2.15 | 0.16 ± 0.01 | −21.13 ± 1.60 | 99.0700% | 14.2% |
| NP15 | 5 | 5.0 | 45.0 | 87.33 ± 2.39 | 0.25 ± 0.01 | −32.80 ± 1.57 | 97.6200% | 13.9% |
| NP16 | 10 | 0.5 | 4.5 | 159.77 ± 1.45 | 0.13 ± 0.01 | −9.00 ± 0.54 | 98.700% | 8.2% |
| NP17 | 10 | 5.0 | 45.0 | 102.17 ± 0.85 | 0.21 ± 0.01 | −11.68 ± 3.69 | 97.200% | 8.1% |
| NP18 | 15 | 0.5 | 4.5 | 113.18 ± 2.49 | 0.16 ± 0.01 | −12.27 ± 0.66 | 98.5900% | 5.8% |
| NP18 | 15 | 5.0 | 45.0 | 80.39 ± 1.37 | 0.23 ± 0.04 | −17.30 ± 1.65 | 97.3200% | 5.7% | being changed every 6 hours. The obtained solution was concentrated by ultrafiltration using a 15-milliliter regenerated cellulose filter (Amicon® Ultra, MWCO 100 kDa) at 4,500 rpm for 20 minutes. The amount of free lysozyme in the flow through was measured by micro-BCA assay. The nanoparticle hydrodynamic diameter and zeta potential was determined by dynamic light scattering (DLS) using a Malvern Zetasizer, and the morphology was analyzed by transmission electron microscopy (TEM). The encapsulation efficiency (EE %) was determined as described in Example 1.

For preparing control nanoparticles including lysozyme: mPEG-b-PCL, DS:mPEG-b-PCL, and lysozyme/DS nanoparticles, each component solution was prepared and characterized as described above. For each of the lysozyme: mPEG-b-PCL, DS:mPEG-b-PCL and lysozyme/DS PEC The encapsulation of lysozyme/DS nanocomplexes within a mPEG-b-PCL nanoparticle was explored by subtracting components from the final nanoparticle formulation (Table 5) while keeping the weight ratio of lysozyme to DS constant (3:1) and also modulating the flow rates of mPEG-b-PCL solution, DS solution, lysozyme solution, and DI water from 1:1:1:1 to 1:1:1:2. For both flow rate conditions, the lysozyme/DS:mPEG-b-PCL nanoparticles were the smallest in hydrodynamic diameter. Each nanoparticle formulation that was lacking a component was larger than all components mixed together. The lysozyme/DS complexes without the mPEG-b-PCL coating had a highly negative zeta potential that decreased upon addition of mPEG-b-PCL coating, together with the more compact size of the particles, suggesting that the complexes were entrapped within the polymer matrix, thus shielding the negative charge.

TABLE 5

Summary of particle sizes, PDIs, and zeta potentials of subtraction component nanoparticles.

| Nanoparticle Components | Polymer to lysozyme mass ratio | Water flow rate (mL/min) | Polymer, DS, and Lysozyme flow rates (mL/min) | Size (nm) | PDI | Zeta potential (mV) |
|---|---|---|---|---|---|---|
| Lys/DS:mPEG-b-PCL | 3 | 0.5 | 0.5 | 118.80 ± 3.10 | 0.21 ± 0.01 | −18.40 ± 0.89 |
| Lys/DS | 3 | 0.5 | 0.5 | 180.30 ± 1.25 | 0.20 ± 0.02 | −63.40 ± 6.79 |
| Lys:mPEG-b-PCL | 3 | 0.5 | 0.5 | 165.30 ± 1.91 | 0.09 ± 0.02 | −23.06 ± 27.05 |
| DS:mPEG-b-PCL | 3 | 0.5 | 0.5 | 150.0 ± 2.85 | 0.12 ± 0.02 | −17.87 ± 0.93 |
| Lys/DS:mPEG-b-PCL | 3 | 4.0 | 2.0 | 92.84 ± 0.86 | 0.22 ± 0.01 | −20.20 ± 0.72 |
| Lys/DS | 3 | 4.0 | 2.0 | 129.90 ± 1.59 | 0.21 ± 0.03 | −60.55 ± 8.98 |
| Lys:mPEG-b-PCL | 3 | 4.0 | 2.0 | 132.20 ± 2.40 | 0.08 ± 0.01 | −0.641 ± 0.25 |
| DS:mPEG-b-PCL | 3 | 4.0 | 2.0 | 135.70 ± 0.10 | 0.10 ± 0.02 | −21.43 ± 0.57 |

Example 5. Preparation and Characterization of Ovalbumin (OVA)/DS:mPEG-b-PCL Nanoparticles by the One-Step Method

Methods

Preparation and Characterization of OVA/DS:mPEG-b-PCL Nanoparticles: Ovalbumin (OVA) was dissolved in DI water at a concentration of 0.5 mg/mL, followed by adjusting its pH to 2.0 by addition of 0.1 M HCl solution. One mL of OVA solution was mixed with equal volumes of DS solution (0.5 mg/mL), $mPEG_{10K}$-b-$PCL_{40K}$ at various concentrations (1.5, 2.5, 5.0, 7.5 mg/mL, dissolved in DMSO), and DI water (pH 7.4). These nanoparticles were characterized as described in Example 1.

Results

Similar to that described in Example 4, the OVA/DS:mPEG-PCL nanoparticles were prepared under different flash mixing conditions by tuning the mass ratio of polymer to OVA as well as the ratio of flow rates of different solutions as listed in Table 5. These nanoparticles exhibited strong negative surface charges with zeta potential ranging from −11.4 to −26.2 mV. The encapsulation efficiencies ranged from 77.9% to 88.6% with little correlation to either the polymer:OVA mass ratio or flow rates.

Example 6. Preparation and Characterization of IgG/DS:mPEG-b-PCL Nanoparticles by the One-Step Method

Methods

Preparation and characterization of IgG/DS:mPEG-b-PCL nanoparticles: Human IgG was dissolved in DI water at a concentration of 0.5 mg/mL, followed by adjusting its pH to 4.0 by addition of 0.1 M HCl solution. The IgG/DS:mPEG-b-PCL nanoparticles were then prepared and characterized using the same procedures as described in the method section of Examples 4 and 5 under the conditions listed in Table 6.

Characterization of Distribution of IgG Within IgG/DS:mPEG-b-PCL Nanoparticles by TEM: IgG was first labeled using Mono-Sulfo-NHS-Nanogold (1.4-nm Au nanoparticles, Nanoprobes) following the manufacturer's protocol. The Au-labeled IgG was then encapsulated using the same method as described above for NP21 illustrated in Table 5. These Au-IgG/DS:mPEG-b-PCL nanoparticles were then imaged using transmission electron microscopy (FEI Tecnai 12) following uranyl acetate (2% w/v) negative staining using the procedure as described in Example 1.

TABLE 5

Summary of particle sizes, PDIs, zeta potentials, EEs and loading levels of OVA in NP19 to NP26.

| Nanoparticle | Polymer to lysozyme mass ratio | Water flow rate (mL/min) | Polymer, DS, and Lysozyme flow rates (mL/min) | Size (nm) | PDI | Zeta potential (mV) | EE (%) | LL (%) |
|---|---|---|---|---|---|---|---|---|
| NP19 | 3 | 0.5 | 0.5 | 130.46 ± 13.53 | 0.35 ± 0.03 | −26.20 ± 1.31 | 77.9% | 15.6% |
| NP20 | 3 | 5.0 | 5.0 | Unstable | Unstable | −20.37 ± 0.40 | 82.3% | 16.5% |
| NP21 | 5 | 0.5 | 0.5 | 114.27 ± 8.89 | 0.219 ± 0.01 | −22.37 ± 0.93 | 84.2% | 12.0% |
| NP22 | 5 | 5.0 | 5.0 | 75.87 ± 4.94 | 0.28 ± 0.03 | −22.50 ± 0.66 | 84.2% | 12.0% |
| NP23 | 10 | 0.5 | 0.5 | 107.13 ± 3.42 | 0.16 ± 0.03 | −16.33 ± 0.57 | 88.0% | 7.3% |
| NP24 | 10 | 5.0 | 5.0 | 68.89 ± 1.43 | 0.16 ± 0.02 | −22.17 ± 1.80 | 88.6% | 7.4% |
| NP25 | 15 | 0.5 | 0.5 | 113.19 ± 1.71 | 0.16 ± 0.02 | −15.20 ± 1.82 | 88.1% | 5.2% |
| NP26 | 15 | 5.0 | 5.0 | 81.63 ± 1.23 | 0.21 ± 0.01 | −11.40 ± 1.05 | 88.6% | 5.2% |

Results

IgG Encapsulation in Nanoparticles: The prepared IgG/DS:mPEG-b-PCL nanoparticles (NP27-NP36) demonstrated that the particle size of the nanoparticles could be varied by tuning the mass ratio of polymer to IgG as well as the flow ratio in a manner similar to that for OVA encapsulation described in Example 5. All the nanoparticles showed negative surface charges with zeta potential ranging from −13.4 to −23.6 mV. The encapsulation efficiencies of IgG ranged from 91.3% to 95.6%, without correlation to either the polymer:IgG mass ratio or flow rates.

days. By day 14, NP19 had about a 38.8% cumulative release with a predicted complete release by day 36.

In Vitro Release Profiles of IgG from NP27: The in vitro release profile of IgG from NP27 was analyzed in PBS (pH 7.4) using the same method. As shown in FIG. 10B, NP27 showed a similar release profile with a mild burst release during the first two days followed by a zero-order release over the next 12 days. By day 14, NP27 had a 26.0% cumulative release of IgG with a predicted full release by day 54. Interestingly, this release profile was moderately slower than OVA from a similar formulation (NP19). These

TABLE 6

| | | | Summary of particle sizes, PDIs, zeta potentials, EEs, and loading levels of IgG NP27 to NP34 | | | | |
|---|---|---|---|---|---|---|---|
| Nanoparticle | Polymer to lysozyme mass ratio | Water flow rate (mL/min) | Polymer, DS, and Lysozyme flow rates (mL/min) | Size (nm) | PDI | Zeta potential (mV) | EE (%) | LL (%) |
| NP27 | 3 | 0.5 | 0.5 | 112.53 ± 1.67 | 0.20 ± 0.01 | −20.23 ± 3.10 | 95.4% | 19.1% |
| NP28 | 3 | 5.0 | 5.0 | 76.63 ± 0.95 | 0.19 ± 0.01 | −23.63 ± 4.80 | 95.6% | 19.1% |
| NP29 | 5 | 0.5 | 0.5 | 89.13 ± 0.85 | 0.18 ± 0.02 | −19.93 ± 3.19 | 94.3% | 13.5% |
| NP30 | 5 | 5.0 | 5.0 | 69.39 ± 1.06 | 0.24 ± 0.02 | −16.90 ± 1.56 | 94.5% | 13.5% |
| NP31 | 10 | 0.5 | 0.5 | 113.30 ± 1.56 | 0.15 ± 0.01 | −16.20 ± 0.62 | 94.9% | 7.9% |
| NP32 | 10 | 5.0 | 5.0 | 72.15 ± 1.41 | 0.20 ± 0.01 | −16.83 ± 0.55 | 91.3% | 7.6% |
| NP33 | 15 | 0.5 | 0.5 | 104.20 ± 1.14 | 0.14 ± 0.01 | −13.43 ± 0.42 | 93.1% | 5.5% |
| NP34 | 15 | 5.0 | 5.0 | 98.18 ± 0.61 | 0.24 ± 0.01 | −15.67 ± 0.21 | 92.7% | 5.5% |

Distribution of IgG Within IgG/DS:mPEG-PCL Nanoparticles: The distribution of IgG-Au (1.4 nm Au nanoparticle conjugated gold) within the IgG/DS-mPEG-b-PCL was determined by TEM (FIG. 9), which showed that above 5:1 (mPEG-b-PCL:IgG) mass ratio, the IgG-Au was distributed throughout the nanoparticle matrix. Image analyses of multiple samples suggest that the relatively even distribution of the IgG-Au appears to be influenced by the mPEG-b-PCL: IgG mass ratio, suggesting that complexes were less densely packed with higher mass ratios and vice-versa.

Example 7. Characterization of In Vitro Release of OVA and IgG from Protein/DS:mPEG-PCL Nanoparticles Prepared by the One-Step Preparation Method Methods One mL of 0.3-0.5 mg/mL OVA/DS:mPEG-b-PCL or IgG/DS:mPEG-b-PCL nanoparticles were added into a 1-mL Float-a-Lyzer dialysis tube (SpectrumLab, MWCO 300 kDa), which was then emerged in a vial containing 6 mL of PBS (containing 0.5 w/v % NaN$_3$, pH 7.4). This entire dialysis device was then placed into a 50-mL centrifuge tube filled with 30 mL of DI water and sealed using Parafilm® to minimize evaporation. The centrifuge tube was placed into a shaker incubator at 200 rpm at 37° C. The 6-mL PBS solution was collected at time points 2 h, 6 h, 12 h, 24 h, and 48 h, and daily thereafter. The collected media samples were frozen at −80° C., lyophilized, and then reconstituted using DI water to give 3× and 6× concentrated protein release samples. Micro-BCA or NanoOrange assays were employed to quantify the amount of released OVA or IgG.

Results: In Vitro Release Profiles

In Vitro Release Profiles of OVA from NP19: The in vitro release profile of OVA from the NP19 was investigated in PBS (pH 7.4) using the dialysis method. As shown in FIG. 10A, NP19 showed a biphasic release profile within the first two days similar to the NPs prepared by the two-step preparation method followed by a zero-order release over 14 data indicate that while the general sustained release kinetics was similar for different proteins, the size of nature of the protein therapeutic may affect the release rate from the nanoparticles.

A single step process of making nanoparticles has been discovered by simultaneously performing steps (a) and (b) of the following process, a surprising result. The first step of the process is (a) forming polyelectrolyte complex by mixing a protein and a counter ion polymer using a first continuous mixing process. The second step of the process is (b) co-precipitating with a biodegradable polymer using a second continuous mixing process. The third step of the process is (c) forming a nanoparticle comprising the protein-polyelectrolyte complex distributed throughout the biodegradable polymer matrix.

The present invention includes a continuous and scalable method to prepare a biodegradable nanoparticle with a uniform distribution of protein PEC throughout the nanoparticle, high payload capacity, and sustained release of protein therapeutics. To regulate protein release and render effective protection and encapsulation, protein therapeutics are complexed into PEC nanoparticles with a polyelectrolyte that carries the opposite charge through a continuous process termed FNC. The resultant PEC nanoparticles (without drying) are then co-precipitated with PEG-b-PLLA or PEG-b-PCL polymer to form a micellar nanoparticle through a CIJ mixer or MIVM using the FNP method. The protein-loaded nanoparticles exhibit negative surface charge, narrow size distribution and tunable particle sizes by changing the weight ratio of protein to polymer ratio and/or flow rates of the input solutions. Most importantly, these nanoparticles enable sustained and prolonged release of proteins. The release rate of these nanoparticles can be tuned via manipulating the weight ratio of protein to polymer or choosing different di-block copolymers. Given the reproducibility and scalability of the nanoparticle production process, as well as the sustained long-term release achieved by these nanoparticles, this platform holds great potential for the preparation of nanoparticles for various of protein therapeutics including many antibody pharmaceutics.

In particular embodiments of the disclosure, a subject may be given, or administered, a nanoparticle of the present invention comprising a pharmaceutical agent, such as a protein, peptide, antibody, chemical, nucleic acid, or a combination thereof. The nanoparticles may be administered to a subject in solid, liquid or aerosol form. The nanoparticles can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

Further in accordance with the present disclosure, the nanoparticles of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, nanoparticles may be combined with the carrier in any convenient and practical manner, i.e., by solution, suspension, emulsification, admixture, encapsulation, absorption and the like. Such procedures are routine for those skilled in the art.

In a specific embodiment of the present invention, nanoparticles of the present invention maybe combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include nanoparticles of the present invention and one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing one or more nanoparticles in a lipid vehicle. For example, the one or more nanoparticles of the present invention may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a nanoparticles of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions including the nanoparticles of the present invention may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alimentary Compositions and Formulations

In one embodiment of the present disclosure, the nanoparticles of the present invention are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the nanoparticles comprising active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions including nanoparticles of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Parenteral Compositions and Formulations

In further embodiments, nanoparticles of the present invention may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,753,514, 6,613,308, 5,466,468, 5,543,158; 5,641,515; and 5,399,363 (each specifically incorporated herein by reference in its entirety).

Solutions of the nanoparticles including active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics Standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

Miscellaneous Pharmaceutical Compositions and Formulations

In other preferred embodiments of the invention, the nanoparticle including an active compound, or agent, may be formulated for administration via various miscellaneous routes, for example, topical (i.e., transdermal) administration, mucosal administration (intranasal, vaginal, etc.) and/or inhalation. Pharmaceutical compositions for topical administration may include the nanoparticles including the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions including the nanoparticles of the present invention may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725, 871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

Kits of the Disclosure

Any of the compositions described herein may be comprised in a kit. In a non-limiting example, a nanoparticle of the present invention (for example, including an agent, or active composition) may be comprised in a kit. The kits may comprise a suitably aliquoted nanoparticles of the present invention and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the one or more nanoparticles of the present invention and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The one or more nanoparticles of the present invention may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder (s). When reagents and/or components are provided as a dry powder, the powder can be reconstituted by the addition of a suitable solvent. It is envisioned that the solvent may also be provided in another container means.

REFERENCES

1. Pagels, R. F.; Prud'homme, R. K. *Journal of Controlled Release.* 2015, 219: 519-535.
2. Patel, A.; Gaudana, R.; Mitra, A. K. *Journal of Microencapsulation.* 2014, 31: 542-550.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A nanoparticle comprising:

a hydrophobic biodegradable polymer core; and a polyelectrolyte complex comprising a pharmaceutical agent and a counter ion polymer wherein the counter ion polymer has an opposite electrostatic charge enabling it to bind electrostatically to the pharmaceutical agent;

wherein the polyelectrolyte complex is uniformly distributed throughout the hydrophobic biodegradable polymer core and wherein the counter ion polymer is selected from the group comprising dextran sulfate (DS), heparin, heparin sulfate, hyaluronic acid, or a combination thereof.

2. The nanoparticle of claim 1 wherein the counter ion polymer is positively charged.

3. The nanoparticle of claim 1 wherein the counter ion polymer is negatively charged.

4. The nanoparticle of claim 1 wherein the pharmaceutical agent is positively charged.

5. The nanoparticle of claim 1 wherein the pharmaceutical agent is negatively charged.

6. The nanoparticle of claim 1 wherein the pharmaceutical agent is selected from the group comprising a protein, peptide, polypeptide, antibody, or a combination thereof.

7. The nanoparticle of claim 1 wherein the hydrophobic biodegradable polymer is a copolymer selected from the group comprising poly(L-lactic acid) (PLLA), poly(glycolic acid) (PGA), poly(lactic-co-glycolic acid) (PLGA), poly(caprolactone) (PCL), their block copolymers with poly(ethylene glycol) (PEG), or a combination thereof.

8. The nanoparticle of claim 1 wherein the hydrophobic biodegradable polymer is poly(ethylene glycol)-b-poly(L-lactic acid) (PEG-b-PLLA); poly(ethylene glycol)-b-poly(caprolactone) (PEG-b-PCL); or a combination thereof.

* * * * *